United States Patent
Paatz et al.

(10) Patent No.: US 6,350,728 B1
(45) Date of Patent: Feb. 26, 2002

(54) COATED ENZYME PREPARATION WITH AN IMPROVED SOLUBILITY

(75) Inventors: Kathleen Paatz; Wilfried Raehse, both of Duesseldorf (DE); Werner Pichler, Kundl (AT); Beatrix Kottwitz, Duesseldorf (DE)

(73) Assignee: Henkel Kommanditgesellschaft Auf Aktien (KGaA), Duesseldorf (DE)

( * ) Notice: Subject to any disclaimer, the term of this patent is extended or adjusted under 35 U.S.C. 154(b) by 0 days.

(21) Appl. No.: 09/319,714

(22) PCT Filed: Dec. 2, 1997

(86) PCT No.: PCT/EP97/06744

§ 371 Date: Jun. 10, 1999

§ 102(e) Date: Jun. 10, 1999

(87) PCT Pub. No.: WO98/26037

PCT Pub. Date: Jun. 18, 1998

(30) Foreign Application Priority Data

Dec. 11, 1996 (DE) .......................................... 196 51 446

(51) Int. Cl.⁷ ........................ C11D 3/386; C11D 17/00; C12N 9/98

(52) U.S. Cl. ........................ 510/392; 510/226; 510/300; 510/320; 510/348; 510/349; 510/441; 510/474; 510/530

(58) Field of Search .................... 510/226, 300, 510/320, 348, 349, 392, 441, 474, 530

(56) References Cited

U.S. PATENT DOCUMENTS

| 3,623,956 A | 11/1971 | Kalabokias | 195/66 |
| 3,623,957 A | 11/1971 | Feidman | 195/66 |
| 3,784,476 A | 1/1974 | Kampen et al. | 252/109 |
| 4,264,738 A | 4/1981 | Stepanov et al. | 435/222 |
| 4,751,003 A | 6/1988 | Raehse et al. | 210/639 |
| 5,719,115 A | * 2/1998 | Paatz et al. | 510/392 |

FOREIGN PATENT DOCUMENTS

| CA | 923 069 | 3/1973 |
| CA | 974 907 | 9/1975 |
| DE | 18 03 099 | 5/1969 |
| DE | 16 17 188 | 2/1971 |
| DE | 16 17 190 | 2/1971 |
| DE | 16 17 232 | 2/1971 |
| DE | 19 40 488 | 2/1971 |
| DE | 20 44 161 | 4/1971 |
| DE | 21 01 803 | 7/1971 |
| DE | 20 32 768 | 1/1972 |
| DE | 21 37 042 | 2/1972 |
| DE | 21 37 043 | 2/1972 |
| DE | 21 21 397 | 11/1972 |
| DE | 43 10 506 | 10/1994 |
| DE | 43 22 229 | 1/1995 |
| DE | 196 44 244 | 4/1998 |
| EP | 0 006 638 | 1/1980 |
| EP | 0 168 526 | 1/1986 |
| EP | 0 200 032 | 11/1986 |
| EP | 0 206 418 | 12/1986 |
| EP | 0 339 426 | 11/1989 |
| EP | WO 93/07260 | * 4/1993 |
| GB | 1 263 765 | 2/1972 |
| JP | 63 32485 | 2/1988 |
| JP | 01 155938 | 6/1989 |
| WO | WO90/13533 | 11/1990 |
| WO | WO91/02792 | 3/1991 |
| WO | WO91/06638 | 5/1991 |
| WO | WO92/11347 | 7/1992 |
| WO | WO93/07260 | 4/1993 |
| WO | WO93/07263 | 4/1993 |
| WO | WO95/02031 | 1/1995 |

OTHER PUBLICATIONS

Database WPI, Class B07, AN89–217408 XP002066911, Dec. 11, 1987.
Database WPI, Class D16, AN88–080330 XP002066912, Jul. 25, 1986.
DIN ISO 2207, Dec. 1983 No Translation.
Tenside 7 (1970), p. 125–132, Jun. 1970 No Translation.

\* cited by examiner

Primary Examiner—Mark Kopec
Assistant Examiner—Brian P. Mruk
(74) Attorney, Agent, or Firm—Wayne C. Jaeschke; Glenn E. J. Murphy

(57) ABSTRACT

An enzyme granule and means for producing the enzyme granule is presented. The enzyme granule is composed of an enzyme, a carrier material, and a coating system of 5 to 70 percent by weight fine-particle inorganic water-insoluble pigment, 45 to 90 percent by weight of a water-soluble organic substance having a melting point of from 40 to 70° C., and 0 to 30 percent by weight of a flow improver. The granule can be produced by mixing an aqueous enzyme liquid with an inorganic or organic carrier material to form an enzyme compound, extruding the enzyme compound, spheronizing the extrudate, and applying an outer coating layer of the coating system listed above to form an enzyme granule having a mean particle size of 0.8 to 1.4 millimeters. The coated enzyme granule has increased storage stability, even coloration, reduced odor, and releases enzyme activity quickly in water. The enzyme granule is useful in solid detergents.

37 Claims, No Drawings

US 6,350,728 B1

COATED ENZYME PREPARATION WITH AN IMPROVED SOLUBILITY

This application is filed under 35 U.S.C. 371 and based on PCT/EP97/06744, filed Dec. 2, 1997.

BACKGROUND OF THE INVENTION

1. Field of the Invention

This invention relates to enzyme granules, to a process for their production and to the use of the granules in solid detergents.

2. Discussion of Related Art

Enzymes, particularly proteases, are widely used in detergents, laundry aids and cleaning products. Normally, the enzymes are not used in the form of concentrates, but in the form of mixtures with a diluent and carrier material. If enzyme preparations such as these are mixed with standard detergents, a considerable reduction in enzyme activity can occur during storage, particularly if bleaching-active compounds are present. Application of the enzymes to carrier salts accompanied by granulation in accordance with DE-OS 16 17 190 or by bonding with nonionic surfactants in accordance with DE-OS 16 17 188 does not product a significant improvement in storage life because the sensitive enzymes in mixtures such as these are generally present on the surface of the carrier. Although the stability of the enzymes in storage can be significantly increased by encapsulating the enzymes with or embedding in the carrier material and subsequently converting them into the desired particle form by extrusion, pressing and marumerizing as described, for example, in DE-PS 16 17 232, in DE-OS 20 32 768 and in DE-ASS 21 37 042 and 21 37 043, enzyme preparations of this type show unsatisfactory solubility properties. The undissolved particles can become caught up in the washing and can soil it or can be discharged into the wastewater without being used. Although the encapsulating agents known from DE-OS 18 03 099, which consist of a mixture of solid acids or acidic salts and carbonates or bicarbonates and which disintegrate on addition of water, improve the solubility of enzyme preparations, they are extremely sensitive to moisture and, accordingly, require additional protective measures.

EP 168 526 describes enzyme granules containing starch swellable in water, zeolite and a water-soluble granulation aid. This document discloses a process for the production of such formulations which essentially comprises concentrating a fermenter solution freed from insoluble constituents, introducing the additives mentioned, granulating the resulting mixture and optionally coating the granules with film-forming polymers and dyes. The process with the proposed additive mixture is advantageously carried out with fermentation solutions which have been concentrated to a relatively high dry matter content, for example of 55% by weight. In addition, the granules thus produced have such a high dissolving or disintegration rate under washing conditions that they disintegrate relatively quickly, to some extent even in storage, and the enzymes are deactivated.

International patent application WO 92/11347 describes enzyme granules for use in granular detergents which contain 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. Additives such as these enable the enzymes to be processed without significant losses of activity.

International patent application WO 93/07263 relates to enzyme-containing granules consisting of a water-soluble or water-dispersible core coated with a vinyl polymer to which a layer of enzyme and vinyl polymer has been applied, the granules having an outer coating of vinyl polymer. The outer coating may also contain pigments. However, the multilayer structure of these enzyme granules makes them relatively difficult to produce.

International patent application WO 95/02031 describes coated enzyme granules of which the coating layer consists of a coating system containing 30% by weight to 50% by weight of fine-particle inorganic pigment, 45% by weight to 60% by weight of an alcohol solid at room temperature with a melting point of 45° C. to 65° C., up to 15% by weight of emulsifier for the alcohol, up to 5% by weight of dispersant for the pigment and up to 3% by weight of water. In view of the presence of relatively large quantities of water-insoluble fatty alcohol, enzyme granules of this type can lead to residue problems when dissolved in water because the presence of the emulsifier is often not sufficient to dissolve the organic components of the coating system.

International patent application WO 93/07260 discloses a process for the production of dust-free enzyme granules which comprises spraying a fermentation broth onto a hydratable carrier material, spraying on a solution of certain coating materials, including fatty acid esters, alkoxylated in alcohols, polyvinyl alcohol, polyethylene glycol, sugar and starch, and evaporating the solvent.

The coating materials used in the documents cited above for the outermost coating layer are normally applied to the enzyme granules in the form of an aqueous dispersion in a fluidized bed dryer. On the one hand, this involves the danger of destruction of at least the surface of the granules by dust abrasion in the fluidized bed which leads to an increased percentage of extremely fine-particle material in the enzyme granules which cannot be used for incorporation in normal particulate detergents because they are not uniformly distributed in the mixture formed and, in addition, enzyme-containing fine dust can lead to allergic reactions in consumers. Accordingly, it is desirable to keep the percentage of fine particles in the enzyme granules as small as possible so that very few have to be removed by sieving or air separation. On the other hand, the use of the coating material in dissolved form is a disadvantage because the solvent applied to the enzyme granules has to be removed again in a separate step.

Accordingly, the problem addressed by the present invention was to develop a coating system which, when uniformly applied to enzyme-containing granules, would counteract surface destruction of the granules, would increase the storage stability of the enzyme by protective coating of the granules as a whole, would enable any color inherent in the uncoated enzyme granules to be covered and would eliminate any potentially troublesome odor of the uncoated granules, probably by reducing the diffusion of the components responsible to the surface of the enzyme granules.

According to the invention, the problem stated above has been solved by enzyme granules suitable for incorporation in detergents, especially particulate detergents, containing enzyme and organic and/or inorganic Garner material and a uniform outer pigment-containing coating layer, characterized in that the outer coating layer consists of a coating system containing 5% by weight to 70% by weight and, more particularly, 10% by weight to 50% by weight of fine-particle inorganic water-insoluble pigment, 45% by weight to 90% by weight and, more particularly, 50% by weight to 85% by weight of a water-soluble organic substance solid at room temperature with a melting point in the range from 40° C. to 70° C. and up to 20% by weight, preferably up to 10% by weight and more preferably from 1% by weight to 5% by weight of flow improvers.

The present invention also relates to a process for the production of enzyme granules suitable for incorporation in particulate detergents with a mean particle size of 0.8 mm to 1.4 mm by extruding an enzyme compound formed by mixing an aqueous enzyme liquid, which may be a concentrated fermentation broth optionally freed from insoluble constituents by microfiltration, with an inorganic and/or organic carrier material as additive, spheronizing the extrudate in a spheronizer, optionally drying and applying an outer coating layer, characterized in that an outer coating layer of a coating system containing 5% by weight to 70% by weight and, more particularly, 10% by weight to 50% by weight of fine-particle inorganic water-insoluble pigment, 45% by weight to 90% by weight and, more particularly, 50% by weight to 85% by weight of a water-soluble organic substance solid at room temperature with a melting point in the range from 40° C. to 70° C. and up to 20% by weight and, more particularly, from 1% by weight to 5% by weight of flow improvers is applied in a fluidized bed of extrudate.

Water-soluble substances in the context of the present invention are understood to be substances of which at least 50 g/l and, more particularly, at least 80 g/l dissolve in water at a temperature of 30° C. Accordingly, fatty alcohols are not included among the water-soluble substances.

The principal component of the coating system, i.e. the water-soluble substance solid at room temperature, is selected in particular from alkoxylated alcohols, fatty acid esters, fatty acid amides and/or hydroxyfatty acid esters. It is preferably an alcohol, more particularly a primary linear alcohol, containing 16 to 22 carbon atoms which is etherified with 45 to 120 and, more particularly, 60 to 110 mole equivalents of alkylene oxide, more especially ethylene oxide. The alcohols mentioned include, in particular, stearyl alcohol, arachidyl alcohol, behenyl alcohol and mono- to tri-unsaturated alcohols of corresponding chain length, the alkoxylated alcohol component mentioned having to have a melting point in the range from 40° C. to 70° C. and, more particularly, in the range from 50° C. to 60° C., the melting point in this context being understood to be the temperature at which 100% of the substance is present in liquid form on heating. Alternatively to or in addition to the alcohol ethoxylates, ethoxylated fatty acid amides and/or ethoxylation products of fatty acid esters or hydroxyfatty acid esters containing 1 to 6 carbon atoms in the alcohol part of the ester, for example ricinoleic acid glyceride, the degree of ethoxylation preferably being from 45 to 120 and, more particularly, from 60 to 110, may also be used. The fatty acid component of the substances mentioned preferably contains 12 to 22 carbon atoms and, more particularly, 16 to 18 carbon atoms. Preferred alkoxylates include ethoxylation products with a so-called narrow homolog distribution (NRE, "narrow range ethoxylates") which are obtained by the process according to European patent EP 339 426 or International patent application WO 90/13533. If desired, the ethoxy groups in the alkoxylation products mentioned can be at least partly replaced by propoxy groups. Where mixtures are used, it is even possible to use mixtures which contain small amounts, normally less than 15% by weight, based on the mixture, of constituents liquid at room temperature providing the mixture as a whole appears solid at room temperature and has a solidification point of 40° C. to 70° C. and, more particularly, in the range from 50° C. to 60°

C. The solidification point is the temperature at which solidification occurs on cooling of material heated to a temperature above the melting point. It may be determined by the method according to DIN ISO 2207 using a rotating thermometer. Substances which, in admixture with the other components of the coating system, give a uniform melt sprayable at temperatures of up to 120° C. are particularly suitable for the production process according to ring the invention. A reference point in this regard is that liquids having viscosities of up to about 500 mPa·s at the temperatures mentioned can generally be readily sprayed and applied to enzyme granules using equipment intended for this purpose, as known for example from German patent application DE 196 44 244.

The coating material preferably contains as an additional component small quantities, preferably 3% by weight to 45% by weight and, more preferably, 4% by weight to 35% by weight, of a compound corresponding to general formula I:

$$R[O(C_nH_{2n}O)_mH]_x \qquad (I)$$

in which R is an organic radical containing at least 2 carbon atoms, preferably 3 to 12 carbon atoms and more preferably 4 to 10 carbon atoms, n is the number 2 or 3, m is a number of 1 to 15 and x has a value of 2 or 3. Components such as these may be prepared in known manner by reacting alcohols $R[OH]_x$ with ethylene oxide and/or propylene oxide and may be part of the above-mentioned component liquid at room temperature. Preferred compounds corresponding to general formula I include those in which both ethoxy groups (n=2) and 1,2-propoxy groups (n=3) are present, the average number of ethoxy groups per hydroxyl group of the alcohol $R[OH]_x$ preferably being up to 10 and the average number of propoxy groups per hydroxyl group of the alcohol $R[OH]_x$ preferably being up to 5. Among these compounds, those in the production of which the alcohol mentioned was reacted first with propylene oxide and then with ethylene oxide are preferably used. Preferred alcohols $R[OH]_x$ include 1,6-hexylene glycol, glycerol and trimethylol propane although 1,2-hydroxyethane may also be used.

In one preferred embodiment of the invention, the coating material system is a mixture of 10% by weight to 35% by weight of water-insoluble inorganic pigment, 20% by weight to 77% by weight and, more particularly, 30% by weight to 71% by weight of the above-mentioned ethoxylated fatty alcohol and 3% by weight to 45% by weight and, more particularly, 4% by weight to 35% by weight of the compound corresponding to general formula 1.

Water-insoluble inorganic pigments with which any troublesome coloration of the enzyme granules can be covered include, for example, calcium carbonate, titanium dioxide (which may be present in the rutile or anatase crystal modification), zinc oxide, zinc sulfide, white lead (basic lead carbonate), barium sulfate, aluminium hydroxide, antimony oxide, lithopone (zinc sulfide/barium sulfate), kaolin, chalk, talcum and/or mica. These pigments are present in such fine-particle form that they can be dispersed in a melt of the other components of the coating system. The mean particle size of such pigments is normally in the range from 0.004 $\mu$m to 50 $\mu$m. Pigments surface-modified with dispersants may also be used. Titanium dioxide pigment, more particularly in rutile form, surface-modified with Al, Si, Zr or polyol compounds, as marketed for example under the trade name of Kronos® 2132 (Kronos-Titan) or Hombitan® R 522 (Sachtleben Chemie GmbH), is preferably used. The Tiona® RLL, AG and VC types marketed by Solvay and the Bayertitan® RD, R, KB and AZ types marketed by Bayer AG may also be used.

Flow improvers are another component of the coating system. Flow improvers are understood to be active substances of which the absence leads to a deterioration in the flow behavior of the coated granules. Suitable flow improvers are, for example, aluminium silicates, zeolites, sodium silicates or silicas which, for application to the enzyme granules, are uniformly mixed in fine-particle form with the other components of the coating system or which may be separately applied after application of the other components of the coating system.

Suitable enzymes are, above all, the proteases, lipases, amylases and/or cellulases obtained from microorganisms, such as bacteria or fungi, proteases produced by bacillus species, either on their own or in combination with amylases, being preferred. They are obtained in known manner by fermentation processes from suitable microorganisms which are described, for example, in DE-OSS 19 40 488, 20 44 161, 21 01 803 and 21 21 397, in US-PSS 3,632,957 and 4,264,738 and in European patent application EP 006 638. The process according to the invention may be used with particular advantage for formulating highly active proteases which are known, for example, from International patent application WO 91/2792 because their storage-stable incorporation in detergents often presents problems and, according to the invention, the formation of unwanted enzyme dusts is avoided. Enzymes are present in the granules according to the invention in quantities of preferably 4% by weight to 20% by weight. If the enzyme granules according to the invention are a protease-containing formulation, their protease activity is preferably 150,000 protease units (PU, as determined by the method described in Tenside 7 (1970), 125) to 350,000 PU and, more particularly, 160,000 PU to 300,000 PU per gram of enzyme granules.

In principle, suitable carrier materials are any organic or inorganic powders which destroy or deactivate the enzymes to be granulated only negligibly, if at all, and which are stable under granulation conditions. Powder-form substances such as these include, for example, starch, cereal flour, cellulose powder, alkali metal aluminosilicate, more particularly zeolite, layer silicate, for example bentonite or smectite, and water-soluble inorganic or organic salts, for example alkali metal chloride, alkali metal sulfate, alkali metal carbonate or alkali metal acetate, sodium and potassium being the preferred alkali metals. A carrier material mixture of water-swellable starch and optionally cereal flour, cellulose powder and/or alkali metal carbonate is preferably used.

The starch swellable in water is preferably corn starch, rice starch, potato starch or mixtures thereof, corn starch being particularly preferred. Swellable starch is present in the enzyme granules according to the invention in quantities of, preferably, 20% by weight to 50% by weight and, more preferably, 25% by weight to 45% by weight.

The cereal flour suitable for use in accordance with the invention, which can contribute towards reducing the odor of the enzyme granules, is in particular a product obtainable from wheat, barley, rye or oats or a mixture of such flours, whole grain flours being preferred. In the context of the invention, a whole grain flour is understood to be a flour which has not been fully ground and which has been produced from whole unshelled grains or which consists at least predominantly of such a product, the remainder consisting of fully ground flour or starch. Commercial wheat flours, such as Type 450 or Type 550, are preferably used. It is also possible to use flours of the cereals leading to the swellable starches mentioned above providing the flours have been produced from the whole grains. It is known that the flour component of the additive mixture provides for a significant reduction in the odor of the enzyme preparation which by far exceeds the reduction in odor achieved by incorporating the same quantities of corresponding starches. The cereal flour is present in the enzyme granules according to the invention in quantities of preferably up to 35% by weight and, more preferably, in quantities of 15% by weight to 25% by weight.

The enzyme granules according to the invention preferably contain 1% by weight to 50% by weight and, more preferably, 3% by weight to 25% by weight, based on the granules as a whole, of a granulation auxiliary system containing alkali metal carboxymethyl cellulose with degrees of substitution of 0.5 to 1 and polyethylene glycol and/or alkyl polyethoxylate. This granulation auxiliary system preferably contains—based on the final enzyme granules—0.5% by weight to 5% by weight of alkali metal carboxymethyl cellulose with degrees of substitution of 0.5 to 1 and up to 3% by weight of polyethylene glycol and/or alkyl polyethoxylate. In a particularly preferred embodiment, at least 0.5% by weight and, more particularly, 0.8% by weight to 2% by weight of polyethylene glycol with an average molecular weight below 1,000 and/or alkyl polyethoxylate containing at least 30 ethoxy groups is present if the granulation auxiliary system contains more than 2% by weight of alkali metal carboxymethyl cellulose. Carboxymethyl cellulose with relatively high degrees of substitution of up to 3 is preferably not present in the granulation auxiliary system.

Phosphated, optionally partly hydrolyzed starches are also suitable granulation auxiliaries. Phosphated starch is understood to be a starch derivative in which hydroxyl groups of the starch anhydroglucose units are replaced by the group —O—P(O)(OH)$_2$ or water-soluble salts thereof, more particularly alkali metal salts, such as sodium and/or potassium salts. The average degree of phosphation of the starch is understood to be the number of esterified oxygen atoms bearing a phosphate group per saccharide monomer of the starch averaged over all the saccharide units. The average degree of phosphation of preferred phosphate starches is in the range from 1.5 to 2.5 because, where phosphated starches such as these are used, far smaller quantities are necessary to obtain a certain granule strength than is the case where carboxymethyl cellulose is used. Partly hydrolyzed starches in the context of the present invention are understood to be oligomers or polymers of carbohydrates which may be obtained by partial hydrolysis of starch using conventional, for example acid- or enzyme-catalyzed processes. The partly hydrolyzed starches are preferably hydrolysis products with average molecular weights of 440 to 500,000. Polysaccharides with a dextrose equivalent (DE) of 0.5 to 40 and, more particularly, 2 to 30 are preferred, DE being a standard measure of the reducing effect of a polysaccharide by comparison with dextrose which has a DE of 100. Both maltodextrins (DE 3–20) and dry glucose sirups (DE 20–37) and also so-called yellow dextrins and white dextrins with relatively high average molecular weights of about 2,000 to 30,000 may be used after phosphation. Contents of 0.1% by weight to 20% by weight and, more particularly, 0.5% by weight to 15% by weight of phosphated starch, based on the final granules, are preferred.

Optional additional constituents of the granulation auxiliary system include other cellulose or starch ethers, such as carboxymethyl starch, methyl cellulose, hydroxyethyl cellulose, hydroxypropyl cellulose and corresponding cellulose mixed ethers, gelatin, casein, tragacanth, maltodextrose, sucrose, invert sugar, glucose sirup or other water-soluble or water-dispersible oligomers or polymers of natural or synthetic origin. Suitable synthetic water-soluble polymers are polyacrylates, poly-methacrylates, copolymers of acrylic acid with maleic acid or compounds containing vinyl groups, polyvinyl alcohol, partially hydrolyzed polyvinyl acetate and polyvinyl pyrrolidone. If the compounds mentioned above are those containing free carboxyl groups, they are normally present in the form of their alkali metal salts, more particularly their sodium salts. Additional granulation auxiliaries such as these may be present in the enzyme granules according to the invention in quantities of up to 10% by weight and, more particularly, in quantities of 0.5% by weight to 8% by weight. Although polyethylene glycols of relatively high molecular weight, i.e. with an average molecular weight above 1,000, may be used as synthetic water-soluble polymers with a dust-binding effect, it is precisely these relatively high molecular weight polyethylene glycols which bring about an unwanted increase in the time required to dissolve the granules, so that these substances are preferably absent altogether from the enzyme granules according to the invention.

The enzyme granules according to the invention are preferably produced from fermenter broths which may be freed from insoluble constituents, for example by microfiltration. The microfiltration process is preferably carried out as crossflow microfiltration using porous tubes with micropores larger than 0.1 mm, flow rates of the concentrate solution of more than 2 m/s and a pressure different relative to the permeate side of less than 5 bar, as described for example in European patent application EP 200 032. The microfiltration permeate is then concentrated, preferably by ultrafiltration optionally followed by evaporation in vacuo. As described in International patent application WO 92/11347, the concentration phase can be carried out in such a way that only relatively low dry matter contents of preferably 5% by weight to 50% by weight and, more preferably, 10% by weight to 40% by weight are obtained. The concentrate is added to a dry powder-form or granular mixture of the additives described above which is preferably prepared beforehand. The water content of the mixture should be selected so that it can be converted into granular particles which are non-tacky at room temperature by treatment with stirring and beating tools and can be plastically deformed and extruded by application of relatively high pressures. The free-flowing compound is then processed in a kneader and an adjoining extruder in basically known manner to form a plastic mass which can assume temperatures of 40° C. to 60° C. and, more particularly, 45° C. to 55° C. as a result of the mechanical treatment. The material leaving the extruder passes through a multiple-bore extrusion die followed by a cutting blade so that it is size-reduced to cylindrical particles of defined size. The diameter of the bores in the multiple-bore extrusion die is 0.7 mm to 1.2 mm and preferably 0.8 mm to 1.0 mm. The particles present in this form may then be dried and coated with the coating system according to the invention. However, it has proved to be of advantage subsequently to spheronize the cylindrical particles leaving the extruder and cutter, i.e. to round off and deflash the particles in suitable units before coating. An arrangement consisting of a cylindrical container with fixed side walls and a friction plate rotatably mounted at its base is used for this purpose. Machines of this type are commercially available under the name of Marumerizer® and are described, for example, in DE-ASS 21 37 042 and 21 37 043. Any dust-fine particles present with a particle size below 0.1 mm and, more particularly, below 0.4 mm and any coarse particles present with a particle size above 2 mm and, more particularly, above 1.6 mm may then be removed by sieving or air separation and optionally returned to the production process. After the spheronizing step, the beads are dried continuously or in batches, preferably using a fluidized-bed dryer, at inflowing air temperatures of preferably 35° C. to 50° C. and, more particularly, at a product temperature of not more than 42° C. to the required residual moisture content of, for example, 4% by weight to 10% by weight and, more particularly, 5% by weight to 8% by weight, based on the granules as a whole, if they previously had higher water contents.

According to the invention, the coating system is applied as an outer coating instead of, after or preferably during the drying process. In one preferred embodiment of the production process according to the invention, the coating system is applied to the extrudate, optionally while cooling, as a heated liquid present at a temperature of 5° C. to 45° C. above the melting point of the organic water-soluble component solid at room temperature. In a preferred embodiment, 5% by weight to 25% by weight of the coating system, based on the final granules, are applied to the enzyme-containing extrudate as an outer coating layer.

The enzyme preparation obtained by the process according to the invention consists of largely rounded, uniformly coated and dust-free particles which generally have a bulk density of about 500 to 900 grams per liter and, more particularly, in the range from 650 to 880 grams per liter. The granules according to the invention are distinguished by very high stability in storage, particularly at temperatures above room temperature and in high atmospheric humidity, and dissolve quickly and completely in the wash liquor. The granules according to the invention preferably release 100% of their enzyme activity in 3 minutes and, more particularly, in 90 seconds to 2 minutes in water at 25° C.

The enzyme granules according to the invention or produced by the process according to the invention are preferably used for the production of solid, more especially particulate, detergents which may be obtained simply by mixing the enzyme granules with other powder components typically encountered in such detergents. For incorporation in particulate detergents, the enzyme granules preferably have average particle sizes of 0.8 mm to 1.2 mm. The granules according to the invention preferably contain less than 2% by weight and, more particularly, at most 1.4% by weight of particles with sizes outside the 0.4 mm to 1.6 mm range.

EXAMPLES

Example 1

A broth harvested after fermentation, as described in International patent application WO 91/2792, containing 75,000 protease units per g (PU/g) was concentrated by decantation and microfiltration in an ultrafiltration module after removal of the fermentation residues. After further concentration by vacuum evacuation, the aqueous enzyme suspension contained 700,000. PU/g. This protease concentrate was mixed with additives (6% by weight sucrose, 4% by weight cellulose, 5% by weight carboxymethyl cellulose with a degree of substitution of 0.65 to 0.75, 16% by weight wheat flour, 36% by weight corn starch and 3% by weight polyethylene glycol with an average molecular weight of 2,000 [quantities based on the mixture formed]), homogenized and then converted into granules in an extruder with a cutting unit. The bore diameter of the multiple-bore extrusion die was 0.85 mm. The length-to-thickness ratio of the granules was 1:1. After spheronizing and drying of the granules, particles smaller than 0.4 mm and larger than 1.66 mm in size were removed by sieving. The particle fraction between 0.4 mm and 1.6 mm was coated with a coating layer in a Glatt type GPCG-5 rotor granulator using a coating melt of 70% by weight of 80x-ethoxylated $C_{16/18}$ fatty alcohol (Lutensol® AT 80, a product of BASF) and 30% by weight of titanium dioxide. The melt kept at 120° C. was sprayed onto the enzyme granules in a quantity of 16% by weight, based on the enzyme granules formed, under the following operating conditions:

| | |
|---|---|
| quantity of enzyme granules used: | 10 kg |
| inflowing air temperature: | 40° C. |
| product temperature: | 42° C. |
| waste air temperature: | 41° C. |
| air volume: | 150 m³/h |
| rotor: | 160 r.p.m. |
| two-component spraying air temperature: | 120° C. |
| feed rate of coating melt: | 50 g/minute. |

The coating material formed a uniform non-porous film on the surface of the granules. To determine the dust abrasion, 60 g of the granules P1 thus produced were introduced into a fluidized bed. The waste air of the fluidized bed flowed through a filter. The quantity of dust collected after a residence time of the enzyme granules under these conditions of 40 minutes corresponds to the quantity of abrasion dust. In the present case, the abrasion dust was negligible at less than 10 mg per filter.

Example 2

The procedure was as in Example 1 using a coating melt consisting of 20% by weight titanium dioxide, 48% by weight 80x-ethoxylated $C_{16/18}$ fatty alcohol, 25% by weight polyethylene glycol and 7% by weight trimethylol propane which had been reacted with 3 equivalents of propylene oxide and 7 equivalents of ethylene oxide per hydroxyl group. In this case, too, granules (P2) with negligible abrasion dust were obtained.

Example 3

To determine the residue-free dissolution of the enzyme granules, 1,000 ml of water (16° dH, kept at 30° C.) were poured into a 2,000 ml glass beaker (tall form), a laboratory stirrer with a propeller stirrer head was fixed centrally 1.5 cm from the bottom of the glass beaker and was set in motion at 800 r.p.m. 8 g of the granules to be tested were scattered in and stirred for 90 seconds. The liquid in the glass beaker was then poured through a sieve (mesh width 0.2 mm) of known weight, the glass beaker was rinsed with a little cold water and the sieve was weighed after drying at 40° C. to constant weight. The sieve residues (double determination) shown in Table 2 were obtained. In addition to the granules P1 and P2 according to the invention, known enzyme granules C1 coated with a coating material consisting of 78% by weight $C_{18}$ fatty alcohol, 4% 40x-ethoxylated $C_{16/18}$ fatty alcohol and 18% by weight titanium dioxide used in the same quantity as before were tested for comparison.

TABLE 2

Sieve residues of the enzyme granules

| Enzyme granules | Sieve residue [% by weight] |
|---|---|
| P1 | 2.5 |
| P2 | 2.5 |
| C1 | 96.0 |

What is claimed is:
1. An enzyme granule comprising:
 (a) an enzyme;
 (b) a carrier material; and
 (c) an outer coating layer consisting of:
  (1) 5 to 70 percent by weight of a fine-particle inorganic water-insoluble pigment;
  (2) 45 to 90 percent by weight of a water-soluble organic substance having a melting point of from 40 to 70° C.;
  (3) up to 20 percent by weight of a flow improver; and
  (4) optionally, a compound corresponding to formula I:

$$R[O(C_nH_{2n}O)_mH]_x \qquad (I)$$

wherein R is an organic radical containing at least 2 carbon atoms, n is the number 2 or 3, m is a number of 1 to 15 and x has a value of 2 or 3.

2. The enzyme granule of claim 1 wherein the fine-particle inorganic water-insoluble pigment is present in the outer coating layer in an amount of 10 to 50 percent by weight.

3. The enzyme granule of claim 1 wherein the water-soluble organic substance is present in the outer coating layer in an amount of 50 to 85 percent by weight.

4. The enzyme granule of claim 1 wherein the water-soluble organic substance has a water solubility at 30° C. of 50 grams per liter or greater.

5. The enzyme granule of claim 4 wherein the water-soluble organic substance has a water solubility at 30° C. of 80 grams per liter or greater.

6. The enzyme granule of claim 1 wherein the flow improver is present in the outer coating layer in an amount of up to 10 percent by weight.

7. The enzyme granule of claim 6 wherein the flow improver is present in the outer coating layer in an amount of 1 to 5 percent by weight.

8. The enzyme granule of claim 1 wherein the water-soluble organic substance comprises:
 (a) a primary linear saturated or unsaturated $C_{16-22}$ alcohol etherified with an average of 45 to 120 mole equivalents of ethylene oxide;
 (b) an ethoxylated fatty acid amide;
 (c) an ethoxylation product of fatty acids or hydroxyfatty acids containing 1 to 6 carbon atoms in the alcohol part of the ester, the degree of ethoxylation being from 45 to 120; or
 (d) a mixture thereof.

9. The enzyme granule of claim 8 wherein the water-soluble organic substance is a primary linear saturated or unsaturated $C_{16-22}$ alcohol etherified with on average 60 to 110 mole equivalents of ethylene oxide.

10. The enzyme granule of claim 1 wherein R in formula I is an organic radical containing 3 to 12 carbon atoms.

11. The enzyme granule of claim 10 wherein R in formula I is an organic radical containing 4 to 10 carbon atoms.

12. The enzyme granule of claim 1 wherein the compound of formula I is prepared by the reaction of alcohols $R[OH]_x$ with ethylene oxide, propylene oxide or mixtures thereof, and contains both ethoxy groups (n=2) and 1,2-propoxy groups (n=3) wherein the average number of ethoxy groups per hydroxyl group of the alcohol $R[OH]_x$ being up to 10 and the average number of propoxy groups per hydroxyl group of the alcohol $R[OH]_x$ being up to 5.

13. The enzyme granule of claim 1 wherein the coating layer consists of:
    (a) 10 to 35 percent by weight of fine-particle inorganic water-insoluble pigment;
    (b) 20 to 77 percent by weight of ethoxylated fatty alcohol; and
    (c) 3 to 45 percent by weight of 4 compound corresponding to general formula I.

14. The enzyme granule of claim 13 wherein the coating layer consists of:
    (a) 10 to 35 percent by weight of inorganic water-insoluble pigment,
    (b) 30 to 71 percent by weight of ethoxylated fatty alcohol; and
    (c) 4 to 35 percent by weight of a compound corresponding to general formula I.

15. The enzyme granule of claim 1 wherein the inorganic water-insoluble pigment is selected from the group consisting of calcium carbonate, titanium dioxide, zinc oxide, zinc sulfide, white lead, barium carbonate, barium sulfate, aluminium hydroxide, antimony oxide, kaolin, chalk, talcum and mica.

16. The enzyme granule of claim 1 wherein the enzyme is a protease, amylase, lipase or cellulase.

17. The enzyme granule of claim 1 wherein the enzyme is a protease with an activity of 150,000 PU to 350,000 PU per gram of enzyme granules.

18. The enzyme granule of claim 17 wherein the enzyme is a protease with an activity of 160,000 PU to 300,000 PU per gram of enzyme granules.

19. The enzyme granule of claim 1 comprising 4 to 20 percent by weight of the enzyme.

20. The enzyme granule of claim 1 comprising 20 to 50 percent swellable starch as the carrier material.

21. The enzyme granule of claim 20 comprising 25 to 45 percent swellable starch as the carrier material.

22. The enzyme granule of claim 1 wherein the carrier material comprises 15 to 25 percent cereal flour.

23. A process for the production of an enzyme granule comprising:
    (a) mixing an aqueous enzyme liquid with an inorganic or organic carrier material to form an enzyme compound;
    (b) extruding the enzyme compound;
    (c) spheronizing the extruded enzyme compound; and
    (d) applying an outer coating layer consisting of:
        (1) 5 to 70 percent by weight of fine-particle inorganic water-insoluble pigment;
        (2) 45 to 90 percent by weight of a water-soluble organic substance having a melting point in the range from 40° C. to 70° C.;
        (3) up to 20 percent by weight of flow improvers,
    wherein the mean particle size of said enzyme granules is 0.8 to 1.4 millimeters.

24. The process of claim 23 wherein the outer coating layer is applied in a fluidized bed.

25. The process of claim 23 wherein the fine-particle inorganic water-insoluble pigment is present in the outer coating layer in an amount of 10 to 50 percent by weight.

26. The process of claim 23 wherein the water-soluble organic substance is present in the outer coating layer in an amount of 50 to 85 percent by weight.

27. The process of claim 23 wherein the water-soluble organic substance has a melting point of from 50 to 60° C.

28. The process of claim 23 wherein the water-soluble organic substance has a water solubility at 30° C. of 50 grams per liter or greater.

29. The process of claim 28 wherein the water-soluble organic substance has a water solubility at 30° C. of 80 grams per liter or greater.

30. The process of claim 23 wherein the flow improver is present in the outer coating layer in an amount of up to 10 percent by weight.

31. The process of claim 23 wherein the flow improver is present in the outer coating layer in an amount of 1 to 5 percent by weight.

32. The process of claim 23 wherein the aqueous enzyme liquid is a concentrated fermentation broth.

33. The process of claim 32 wherein the aqueous enzyme liquid is freed from insoluble constituents by microfiltration.

34. The process of claim 23 wherein the enzyme granule comprises 5 to 25 percent by weight of the outer coating layer.

35. The process of claim 23 wherein the coating system is applied to the extrudate as a liquid at a temperature of 5 to 45° C. above the melting point of the water-soluble organic substance.

36. The process of claim 24 wherein the enzyme granule has a bulk density of 500 to 900 grams per liter.

37. The process of claim 36 wherein the enzyme granule has a bulk density of 650 to 880 grams per liter.

* * * * *

UNITED STATES PATENT AND TRADEMARK OFFICE
CERTIFICATE OF CORRECTION

PATENT NO.     : 6,350,728 B1
DATED          : February 26, 2002
INVENTOR(S)    : Paatz et al.

It is certified that error appears in the above-identified patent and that said Letters Patent is hereby corrected as shown below:

Column 11,
Line 13, after "weight of", delete "4", and insert therefor -- a --.

Signed and Sealed this

Second Day of September, 2003

JAMES E. ROGAN
*Director of the United States Patent and Trademark Office*